US011833178B2

(12) United States Patent
Cryan et al.

(10) Patent No.: US 11,833,178 B2
(45) Date of Patent: Dec. 5, 2023

(54) ***BIFIDOBACTERIUM LONGUM* FOR TREATING OBESITY AND WEIGHT MANAGEMENT**

(71) Applicants: UNIVERSITY COLLEGE CORK—NATIONAL UNIVERSITY OF IRELAND, CORK, Cork (IE); AGRICULTURE AND FOOD DEVELOPMENT AUTHORITY (TEAGASC), Carlow (IE)

(72) Inventors: John Cryan, Cork (IE); Ted Dinan, Cork (IE); Catherine Stanton, Cork (IE); Harriet Schellekens, Cork (IE); Cristina Torres, Cork (IE); Bernard Roy, Cork (IE)

(73) Assignees: UNIVERSITY COLLEGE CORK—NATIONAL UNIVERSITY OF IRELAND, CORK, Cork (IE); AGRICULTURE AND FOOD DEVELOPMENT AUTHORITY (TEAGASC), Carlow (IE)

( * ) Notice: Subject to any disclaimer, the term of this patent is extended or adjusted under 35 U.S.C. 154(b) by 2 days.

(21) Appl. No.: 16/641,954

(22) PCT Filed: Aug. 27, 2018

(86) PCT No.: PCT/EP2018/072988
§ 371 (c)(1),
(2) Date: Feb. 25, 2020

(87) PCT Pub. No.: WO2019/038449
PCT Pub. Date: Feb. 28, 2019

(65) Prior Publication Data
US 2020/0281992 A1 Sep. 10, 2020

(30) Foreign Application Priority Data
Aug. 25, 2017 (EP) .................................... 17187989

(51) Int. Cl.
*A61K 35/745* (2015.01)
*C12N 1/20* (2006.01)
*A23L 33/135* (2016.01)
*A61P 3/04* (2006.01)
*A61P 3/10* (2006.01)

(52) U.S. Cl.
CPC .......... *A61K 35/745* (2013.01); *A23L 33/135* (2016.08); *A61P 3/04* (2018.01); *A61P 3/10* (2018.01); *C12N 1/20* (2013.01); *A23Y 2300/55* (2013.01)

(58) Field of Classification Search
None
See application file for complete search history.

(56) References Cited

U.S. PATENT DOCUMENTS

| 2012/0244125 | A1 | 9/2012 | Verdu de Bercik et al. |
| 2016/0143963 | A1 | 5/2016 | Martorell Guerola et al. |
| 2017/0058270 | A1* | 3/2017 | Garcia-Garcia ........ A61P 29/00 |
| 2019/0111090 | A1 | 4/2019 | Kiely et al. |

OTHER PUBLICATIONS

Papadimitriou et al. Front. Microbiol. 6: 1-28, 2015.*
Barrett et al. Arch Dis Child Fetal Neonatal Ed. 100: F405-F410, first published online Apr. 20, 2015.*
Fuentes Cristine Torres et al, "Identification of Novel Probiotics to Modify Appetite and Satiety Directly Targeting the Ghrelin Receptor", Biosis Apr. 2016 (Apr. 2016), Database accession No. PREV201700781485 Retrieved from the Internet: URL:Biosciences Information Service, Philadelphia, PA, US XP002776145.
Nazarii Kobyliak et al, "Probiotics in prevention and treatment of obesity: a critical view", Nutrition & Metabolism, vol. 13, No. 1, Feb. 20, 2016 (Feb. 20, 2016), XP055429690.
Silvia Arboleya et al, "Gene-trait matching across the pan-genome reveals considerable diversity in carbohydrate catabolism among human infant strains", BMC Genomics, Biomed Central Ltd, London, UK,vol. 19, No. 1, Jan. 8, 2018 (Jan. 8, 2018), p. 1-16, XP021252288 DOI: 10.1186/S12864-017-4388-9.
Written Opinion for PCT/EP2018/072988, dated Nov. 8, 2018, European Patent Office, Rijswijk, NL.
International Search Report for PCT,EP2018/072988 dated Nov. 8, 2018, European Patent Office, Rijswijk, NL.

* cited by examiner

*Primary Examiner* — S. Devi
(74) *Attorney, Agent, or Firm* — Stephen J. Weyer, Esq.; Stites & Harbison, PLLC

(57) ABSTRACT

A strain of *Bifidobacterium longum* APC 1472 is described. The strain has weight lowering effects in-vivo, achieved through inducing satiety via decreased internalisation of the Ghrelin receptor, and therefore, decreased constitutive activity. Moreover, the strain also showed a trend towards decreased ghrelin receptor hypothalamic expression in HFD-fed mice when compared with vehicle control group. The strain also improves glucose tolerance and decreased insulin plasma levels in mice, indicating the strain in the prevention and/or treatment of Type II diabetes, especially in obese individuals.

12 Claims, 8 Drawing Sheets
Specification includes a Sequence Listing.

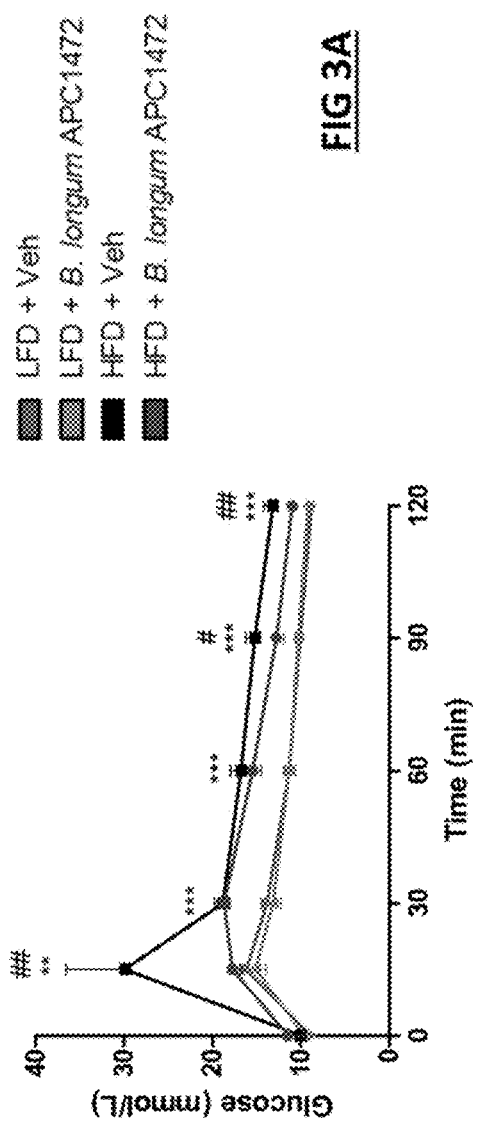
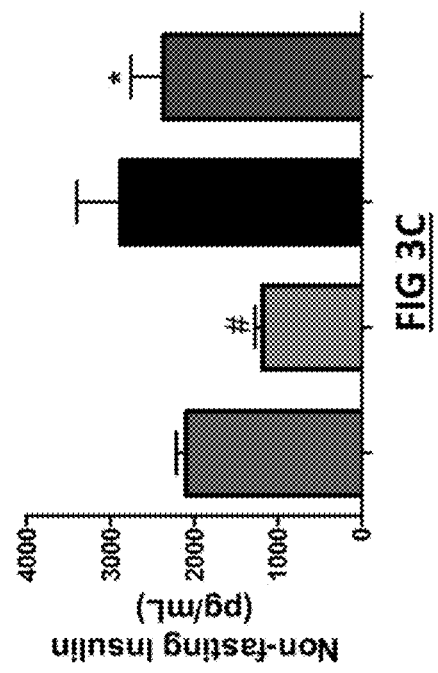
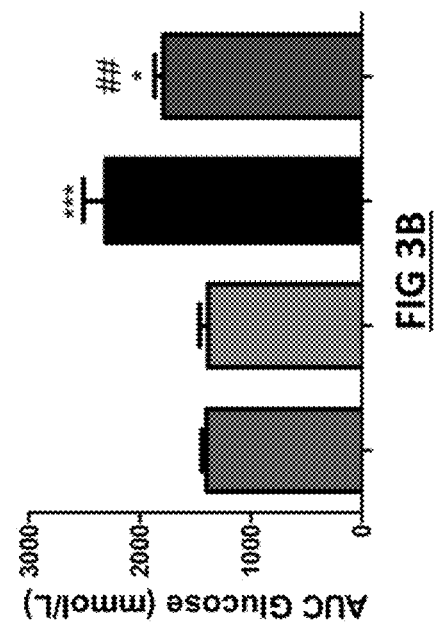

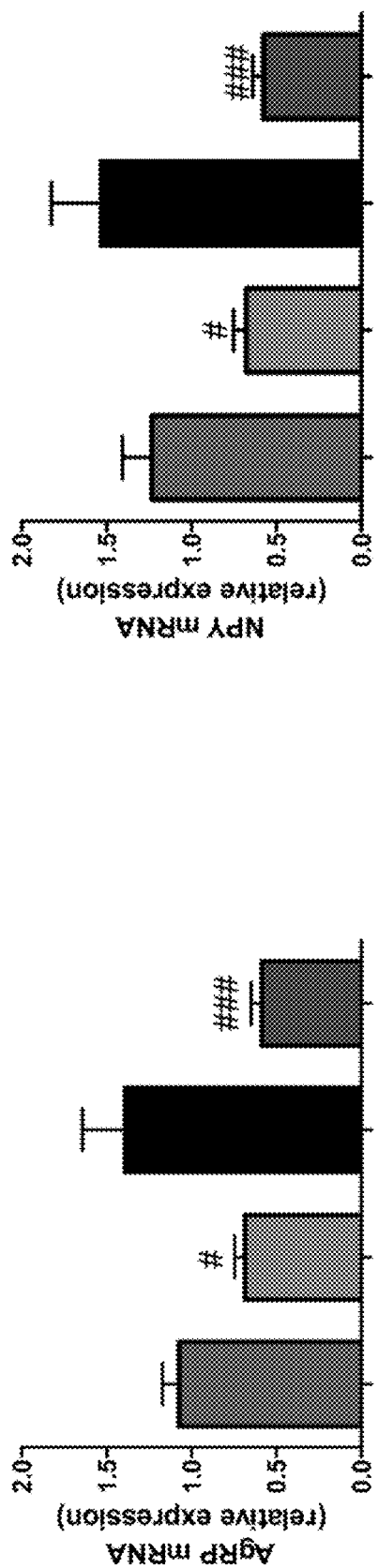
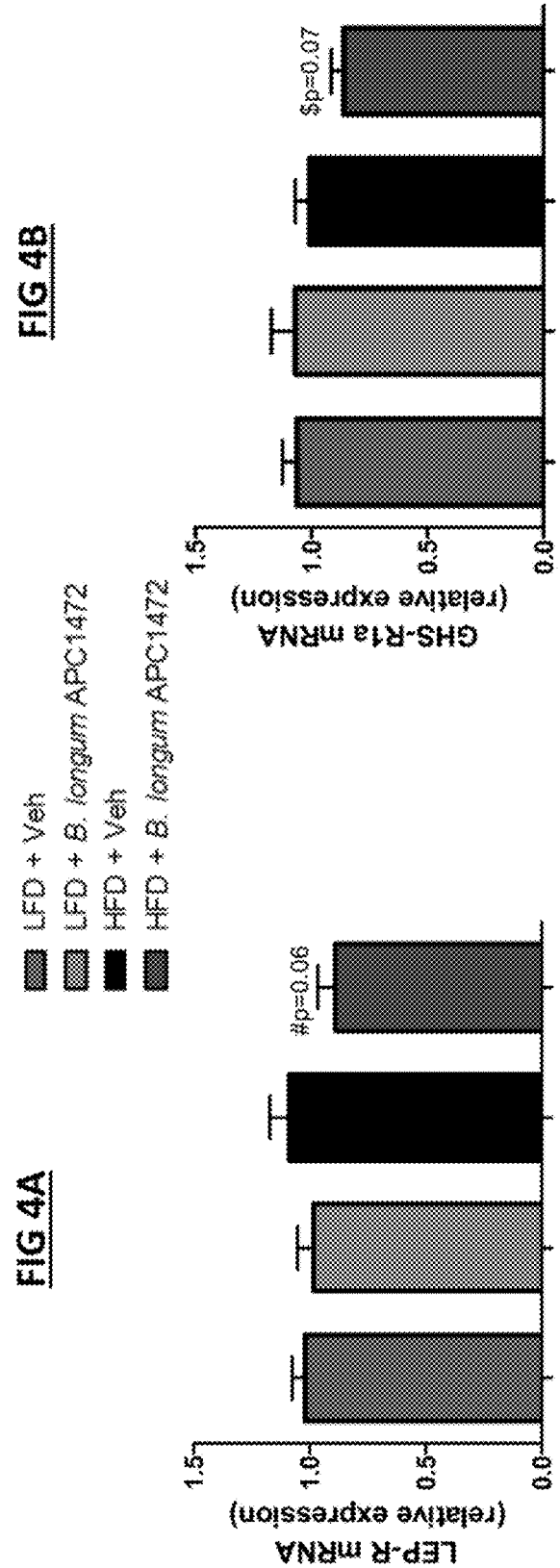

BIFIDOBACTERIUM LONGUM FOR TREATING OBESITY AND WEIGHT MANAGEMENT

FIELD OF THE INVENTION

The present invention relates to an isolated strain of *Bifidobacterium longum*, compositions comprising the strain, and uses of the strain or composition to treat obesity and manage weight in a subject. The invention also relates to a use of the bacterium or composition to treat Type 2 diabetes, prevent stress and anxiety, and improve glucose tolerance, in a subject, especially an overweight or obese subject.

BACKGROUND TO THE INVENTION

Current pharmacologic anti-obesity treatments lack efficacy and have shown severe side effects, highlighting the urgent need for novel strategies contributing to the maintenance of a healthy weight. Probiotics are an example of a natural product and if efficacious anti-obesity probiotics can be identified, these would be safer for consumers than synthetic therapeutics.

WO2017/097987 describes a strain of *Bifidobacterium longum* AH1362 capable of increasing energy excretion in a subject.

WO2011/039176 describes a strain of *Bifidobacterium longum* BL999 capable of reducing weight gain in a high fat diet fed mouse over a seven week period. The weight reduction effect is achieved through increased pAMPk activity, indicating induction of metabolic effects on adipose and skeletal muscle tissue.

Thus, the prior art describes probiotic approaches for achieving weight reduction, both of which elicit their effects at a post-prandial level without having any effect on food intake.

It is an object of the invention to overcome at least one of the above-referenced problems.

SUMMARY OF THE INVENTION

The present invention addresses the need for an anti-obesity treatment that is free of side effects, based on a probiotic approach. The Applicant has discovered a specific strain of *Bifidobacterium longum*, *Bifidobacterium longum* APC1472, that is capable of significantly decreasing body weight, and adiposity at key anatomical sites, compared to vehicle controls in high fat diet model mice. The bacterium significantly decreased levels of leptin and significantly reduced the level of internalisation of the "hunger hormone" ghrelin receptor, indicating that the anti-obesity effect is at least partially mediated through increased satiety in a subject. This is an advantage over the methods of the prior art, which act at a metabolic level in a post-prandial manner and do not have any effect on the level of food intake. The strain also improved glucose tolerance and decreased insulin plasma levels in mice, indicating the strain in the prevention and/or treatment of Type II diabetes, especially in obese individuals. The anti-diabetic effect is supported by the additional finding that the strain increased the expression of the IRS1 (insulin receptor substrate) gene. Moreover, the treatment also decreased other orexigenic neuropeptides expression in the hypothalamus such as NPY and Argp that may have also contributed to the satiety effect, and decreased the hypothalamic Ghrelin receptor expression in HFD-fed mice (when comparing only HFD groups . . . so Mann Whitney test) (p=0.077)

According to a first aspect of the present invention, there is provided an isolated *Bifidobacterium longum* APC1472 strain as deposited with the National Collection of Industrial, Food and Marine Bacteria under the Accession No. NCIMB 42795 on 1 Aug. 2017 (hereafter "APC1472 strain" or "strain of the invention" or "deposited strain"). The *Bifidobacterium longum* APC1472 strain was deposited with the National Collection of Industrial Food and Marine Bacteria (NCIMB Ltd, Ferguson Building, Craistone Estate, Bucksburn, Aberdeen, AB21 9YA), under accession No. NCIMB 42791 on 1 Aug. 2017 (herein "the Deposit") in accordance with the Budapest Treaty biological deposit requirements. All restrictions imposed by the depositor on the availability to the public of the deposited material will be irrevocably removed upon the granting of the patent.

The invention also relates to a supernatant or cell material derived from the isolated APC1472 strain.

The invention also provides a composition comprising the isolated APC1472 strain, or a supernatant or cell material derived from the isolated APC1472 strain.

The composition may be a pharmaceutical composition, and may include a suitable pharmaceutical excipient. The composition may be provided in a unit dose form suitable for oral administration, i.e. a tablet or capsule.

The composition may be a food or beverage product, or a nutritional supplement.

The composition may comprise a probiotic material. The composition may comprise a prebiotic material.

The composition may comprise an additional probiotic bacterium.

The strain in the composition may be viable or non-viable, and may comprise a strain extract (i.e. bacterial cell lysate) or supernatant derived from the strain. The extract or supernatant may be in any physical form, for example liquid or dried.

The composition may comprise at least 106 cfu per gram of composition.

The composition may be solid or liquid. The composition may comprise a carrier for oral delivery. The carrier may be in the form of tablet, capsule, powder, granules, microparticles or nanoparticles. The carrier may be configured for targeted release in the intestine (i.e. configured for gastric transit and ileal release). The carrier may be configured for controlled release in the intestine (i.e. configured for gastric transit and ileal release).

The composition may be dried or lyophilised.

The invention also relates to a method of treating or preventing obesity in a subject, typically a subject in need thereof, comprising a step of administering a therapeutically effective amount of bacterium or composition of the invention to the subject.

The invention also relates to a method of reducing weight gain in a subject, typically a subject in need thereof, comprising a step of administering a therapeutically effective amount of bacterium or composition of the invention to the subject.

The invention also relates to a method of reducing visceral or subcutaneous fat in a subject, typically an overweight or obese subject, comprising a step of administering a therapeutically effective amount of bacterium or composition of the invention to the subject.

The invention also relates to a method of increasing satiety in a subject, typically a subject in need thereof, comprising a step of administering a therapeutically effective amount of bacterium or composition of the invention to the subject.

The invention also relates to a method of treating or preventing a metabolic disorder characterised by obesity in a subject, typically a subject in need thereof, comprising a step of administering a therapeutically effective amount of bacterium or composition of the invention to the subject.

The invention also relates to a method of treating or preventing Type-2 diabetes in a subject, typically a subject in need thereof, comprising a step of administering a therapeutically effective amount of bacterium or composition of the invention to the subject.

The invention also relates to a method of improving glucose intolerance in a subject, typically a subject in need thereof, comprising a step of administering a therapeutically effective amount of bacterium or composition of the invention to the subject.

The invention also relates to a method of treating or preventing or reducing the incidence of stress, anxiety or depression in a subject, typically a subject in need thereof, comprising a step of administering a therapeutically effective amount of bacterium or composition of the invention to the subject.

The invention also relates to a method of treating or preventing a sleep disorder in a subject, typically a subject in need thereof, comprising a step of administering a therapeutically effective amount of bacterium or composition of the invention to the subject.

In one embodiment, the sleep disorder is a form of insomnia, typically primary insomnia, for example primary insomnia characterised by sleep onset or sleep maintenance problems, or non-restorative sleep. In one embodiment, the subject is a person with ADHD, typically a child or teenager with ADHD.

The invention also relates to a method of treating or preventing inflammation in a subject (for example an inflammatory disorder, especially a gut inflammatory disorder such Inflammatory Bowel Disease, Crohns Disease, or the like), typically a subject in need thereof, comprising a step of administering a therapeutically effective amount of bacterium or composition of the invention to the subject. In one embodiment, the inflammation is gut inflammation associated with an inflammatory disorder of the gut, for example Inflammatory Bowel Disease or a similar condition.

The invention also relates to a method of enhancing gut hormone profile, or treating or preventing a disease or condition characterised by dysregulated gut hormone profile, in a subject and typically a subject in need thereof, comprising a step of administering a therapeutically effective amount of bacterium or composition of the invention to the subject.

The invention also relates to a method of improving gut health is a subject, typically a subject in need thereof, comprising a step of administering a therapeutically effective amount of bacterium or composition of the invention to the subject. In one embodiment, the method is a method of enhancing the diversity of the gut microbiota of the subject, or improving the stability of the gut microbiota in the subject.

The invention also relates to a method of improving the lipid profile in a subject, typically a subject in need thereof, comprising a step of administering a therapeutically effective amount of bacterium or composition of the invention to the subject. In one embodiment, the method is a method of reducing total plasma cholesterol, triglyceride, or low density lipoprotein (LDL) levels, or increasing total high density lipoprotein (HDL) levels, in the subject.

The invention also provides a method of producing a supernatant from an isolated *Bifidobacterium longum* APC1472 strain comprising a step of culturing the isolated strain and separating the supernatant from the strain.

The invention also provides a method of producing an extract from an isolated *Bifidobacterium longum* APC1472 strain comprising a step of lysing the cell and separating the cell extract from lysed cell material.

The invention also provides a supernatant or bacterial material or extract (for example a cell lysate) formed according to the method of the invention.

In one embodiment, the subject is overweight. In one embodiment, the subject is obese.

In one embodiment, the subject is an adult. In one embodiment, the subject is an infant.

In one embodiment, the composition is selected from a pharmaceutical composition, a food, a food supplement, or a beverage.

Other aspects and preferred embodiments of the invention are defined and described in the other claims set out below.

BRIEF DESCRIPTION OF THE FIGURES

FIG. 1A are images that depict the following different treatments: untreated control (assay medium), ghrelin (0.5 µM), [D-Arg1, D-Phe5, D-Trp7,9, Leu11]-substance P (SP-analogue) (0.5 µM), and different bacterial strains supernatants. FIG. 1B is a graph representing the mean±SEM of quantified fluorescence intensity (15 pictures per treatment) of perinuclear GHS-R1a-EGFP receptor from 4 independent experiments with each treatment at least in duplicate. Cells were exposed to the different treatments for 1 hour with or without subsequent ghrelin addition for another hour. FIG. 1C is a graph of β-arrestin-1 recruitment analysis expressed as relative light units (RLU) after exposure to SP-analogue (0.5 µM) and *B. longum* APC1472 supernatant for 1 hour with or without subsequent ghrelin addition for another hour. The graph of FIG. 1C represents the mean±SEM of two independent experiments with each treatment in triplicate. Data are significant different (p≤0.05) accordingly to Kruskal Wallis test followed by Bonferroni p value correction for multiple comparisons. *indicates significantly increased vs untreated control (comparisons between controls and non-ghrelin treated samples) $indicates significantly decreased vs untreated control (comparisons between controls and non-ghrelin treated samples) #indicates significantly decreased vs ghrelin control (comparisons between all ghrelin treated samples).

FIG. 2A is a graph for kinetic evolution of body weight gain, FIG. 2B is a graph showing total body weight gain and FIG. 2C is a graph showing mesenteric, FIG. 2D is a graph for retroperitoneal, FIG. 2E is a graph showing subcutaneous and FIG. 2F is a graph showing epididymal fat depots accumulation (% of total body weight) in control mice treated with drinking water containing sterile PBS (2% vol/vol) and glycerol (0.5% vol/vol) and fed a control low-fat diet (LFD) (N=10) or a high-fat diet (HFD) (N=9) and in mice treated with *B. Longum* APC1472 in drinking water (2×108 CFU/mL) and fed a LFD (N=9 in A, B, C, E and F; N=8 in D) or a HFD (N=9 in A, B, C, D, and F; N=8 in E) for 15 (A, and B) or 16 weeks (C, D, E and F). Data are shown as means±SEM. Data are significant different (p≤0.05) accordingly to Repeated Measures ANOVA (A) or two-way ANOVA followed by LSD post-hoc test (B, C, D, E and F). * indicates significant diet treatment effect (p≤0.05) and #indicates significant B. *Longum* APC1472 treatment effect.

FIGS. 3A-3G are graphs showing *Bifidobacterium longum* APC1472 improved glucose tolerance, leptin plasma levels and stress-induced corticosterone circulating levels in high-fat diet-induced obesity. FIGS. 3A and 3B are graphs showing tolerance test (GTT) glucose curve (included times: 15', 30', 60', 90' and 120') and area under the curve (AUC) after 1 g/kg glucose challenge, FIGS. 3C-3D are graphs for non-fasting and fasting insulin plasma levels, FIG. 3E is a graph showing fasting leptin plasma levels, FIG. 3F is a graph showing epididymal fat insulin receptor substrate (IRS)-1 mRNA expression and FIG. 3G is a graph showing fasting-induced corticosterone plasma in control mice treated with drinking water containing sterile PBS (2% vol/vol) and glycerol (0.5% vol/vol) and fed a control low-fat diet (LFD) (N=10 in A, B, C, E, F and G) or a high-fat diet (HFD) (N=9 in A, B, C, D, E and G; N=8 in F) and in mice treated with B. *Longum* APC1472 in drinking water (2×10$^8$ CFU/mL) and fed a LFD (N=9 in A, B, C, D, E and F; N=8 in G) or a HFD (N=9 in A, B, C, D, E and F; N=8 in G) for 15 (A, B, C) or 16 weeks (D, E, F and G). Data are shown as means±SEM. Data are significant different (p≤0.05) accordingly to Repeated Measures ANOVA (A) or two-way ANOVA followed by LSD post-hoc test (B, C, D, E, F and G). * indicates significant diet treatment effect (p≤0.05) and #indicates significant B. *Longum* APC1472 treatment effect.

FIGS. 4A-4D are graphs showing *Bifidobacterium longum* APC1472 effects on orexigenic neuropeptides and gut hormones receptors expression in the hypothalamus. mRNA expression of orexigenic markers Agouti-related protein (AgRP) (FIG. 4A) and neuropeptide Y (NPY) FIG. 4B, leptin receptor FIG. 4C and ghrelin receptor FIG. 4D measured in the hypothalamus of mice treated with drinking water containing sterile PBS (2% vol/vol) and glycerol (0.5% vol/vol) and fed a control low-fat diet (LFD) (N=9 in A; N=10 in B, C and D) or a high-fat diet (HFD) (N=9) and in mice treated with B. *Longum* APC1472 in drinking water (2×10$^8$ CFU/mL) and fed a LFD (N=9) or a HFD (N=9) for 16 weeks. Data are shown as means±SEM. Data are significant different (p≤0.05) accordingly to two-way ANOVA followed by LSD post-hoc test (A, B, and C) and to Mann-Whitney U test (D). * indicates significant diet treatment effect (p≤0.05), #indicates significant B. *Longum* APC1472 treatment effect, $ indicates significant B. *Longum* APC1472 treatment effect in HFD-fed mice.

DETAILED DESCRIPTION OF THE INVENTION

Figure 1B:
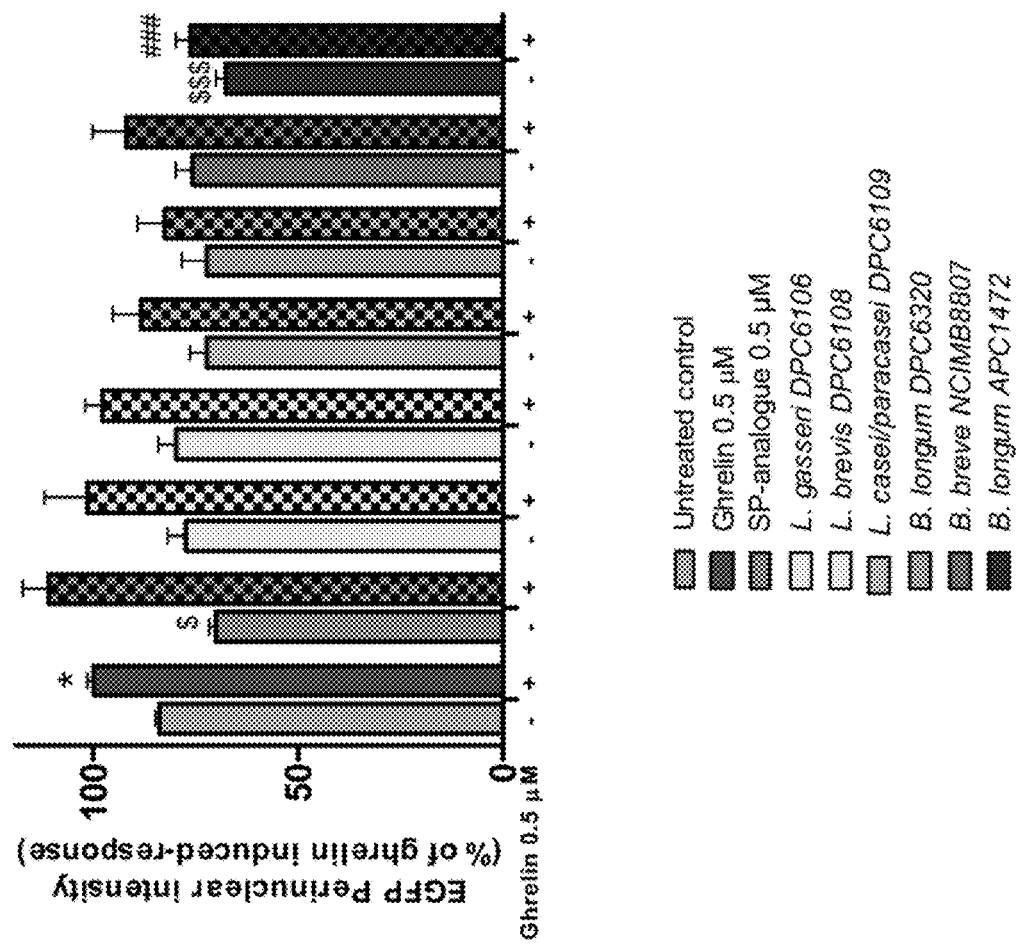
FIGS. 1A-1C are directed to identification of *Bifidobacterium longum* strain with ghrelin signalling modulation activity in HEK293a cells stably expressing the GHS-R1a with a C-terminal enhanced green fluorescent protein (EGFP) tag.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

Disease and Therapy

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent (i.e. bacterium or composition of the invention) defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

"Overweight" as applied to an adult human means a Body Mass Index (BMI) of 25-29.9.

"Obese" or "Obesity" as applied to an adult human means a BMI of 30 or greater.

"Body Mass Index" or "BMI" is calculated as [weight (kg)/height (m2)×703].

"Reducing weight gain" refers to a reduction in the rate at which a subject gains weight. In one embodiment, it refers to a cessation of weight gain (i.e. the subject stops gaining weight and their weight remains substantially static or even reduces over time).

"Increasing satiety" refers to inducing a feeling of fullness in a subject as a result of administration of an effective amount of a strain or composition of the invention. It could also be described as "reducing hunger".

"Metabolic disorder" refers to pre-diabetes, diabetes; Type-1 diabetes; Type-2 diabetes; metabolic syndrome; obesity; diabetic dyslipidemia; hyperlipidemia; hypertension; hypertriglyceridemia; hyperfattyacidemia; hypercholerterolemia; and hyperinsulinemia.

"Type 2 Diabetes" refers to a long term metabolic disorder that is characterised by high blood sugar, insulin resistance, and a relative lack of insulin. It primarily occurs as a result of obesity and lack of exercise. It comprises about 90% of all forms of diabetes, the other forms being Type 1 diabetes and gestational diabetes.

"Glucose intolerance" as applied to a subject means a subject that exhibits a fasting blood glucose level of above 6.0 mmol/L or a blood glucose level of over 7.8 mmol/L after consuming 75 g of glucose. Symptoms of glucose intolerance include thirst, dry mouth, extreme tiredness, blurred vision, drowsiness, frequent need to urinate, and loss of muscle mass. The strain or compositions of the invention can improve glucose intolerance in a subject, for example by having a causative effect on the condition, or addressing one or more symptoms of the condition. Treatment of glucose intolerance may also include dietary or lifestyle changes, including weight loss, increased level of exercise, and possibly also pharmaceutical intervention. Current therapies for glucose intolerance includes metformin therapy.

"Inflammatory disorder of the gut" refers to chronic inflammatory disorders of the gastrointestinal tract, including Inflammatory bowel diseases (IBD) such as Cronh's disease and ulcerative colitis. Symptoms of IBD include frequent bloody diarrhoea, abdominal cramping, anorexia, abdominal distension, and emesis.

"Inflammatory disorders" refers to a disease or condition characterised by the subjects immune system attacking the body's own cells or tissue resulting in chronic pain, redness, swelling, stiffness and damage to normal tissues. Examples include rheumatoid arthritis, Gout, Lupus, Inflammatory bowel disease, Vasculitis, Myositis, Sclerodema, Ankylosing Spondylitis and Sjogren's Syndrome.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

Bifidobacterium longum APC1472 Strain

"Bifidobacterium longum APC1472 strain" refers to the strain of bacteria deposited with the National Collection of Industrial, Food and Marine Bacteria (Ferguson Building, Craibstone Estate, Bucksburn, Aberdeen AB219YA, UK) under the Accession No. NCIMB 42795 on 1 Aug. 2017. The Deposit was made by the APC Microbiome Institute, an Institute forming part of University College Cork, National University of Ireland, Cork, and having an address of UCC, Cork, Ireland. The term is intended to include the strain in a viable or non-viable form, or mixtures of viable and non-viable bacteria. The strain may be provided in any format, for example as a liquid culture (or supernatant derived from a liquid culture), or cell material or extract derived from the strain or a culture of the strain, or in a dried or freeze-dried format. The invention may also employ growth media in which the strain of the invention was grown, or cell lysates generated using the strain of the invention. The term also includes mutants and variants of the deposited strain that are substantially identical, genetically and phenotypically, to the deposited strain and retain the activity of the deposited strain. Thus, the term includes derivatives of the strain that have been genetically engineered to modify the genome of the strain, typically without fundamentally altering the functionality of the organism, for example engineered for heterologous expression of a nucleic acid, or engineered to overexpress an endogenous gene, or engineered to silence a gene, to produce a recombinant or transformed strain of the invention. Genetic modifications may be carried out using recombinant DNA techniques and reagents, including gene editing technologies such as CRISP-Cas9 techniques (see below). The term also includes variants of the strain having natural or spontaneous genetic alterations. The term is also intended to encompass variant strains obtained by serial passage of the isolated strain of the invention. The variant generally has a 16S rRNA amplicon (fragment) sequence that is identical or substantially identical with the deposited strain, for example at least 99.1%, 99.2%, 99.3%, 99.4%, 99.5%, 99.6%, 99.7%, 99.8% or 99.9% identical with the deposited strain. Sequence homology can be determined using an online homology algorithm "BLAST". The sequence of the 16s rRNA amplicon for the Deposited Strain is provided in Annex 1 below (SEQUENCE ID NO: 1). The antibiotic susceptibility profile of the Deposited Strain is provided in Table 1 below.

TABLE 1

Antibiotic Susceptibility Profile of Bifidobacterium longum APC1472 strain

| Strain | Gm | Sm | Tc | Em | Cl | Cm | Am | Va |
|---|---|---|---|---|---|---|---|---|
| B. longum APC1472 | 16-64 | 64-128 | 1 | 0.06-0.12 | 0.06-0.12 | 2 | 2 | 0.5 |

Gm: Gentamicin, Sm: Streptomycin, Tc: Tetracycline, Em: Erythromycin, Cl: Clindamycin, Cm: Chloramphenicol, Am: Ampicillin, Va: Vancomycin
MICs (in μg/mL) for Bifidobacterium longum ssp. longum APC1472, for antibiotics with published EFSA cut-off values. Values shown are the range of MICs for duplicate experiments Compositions and Foods The invention also relates to a composition comprising a strain of the invention. The composition may be a pharmaceutical composition, or a food composition, or a dietary supplement composition. The term "food" refers to a man-made food product including beverages, food additives and food supplements. Examples of foods include dairy products such as milk, yoghurt, cheese, cheese food, dairy powders, probiotic formulations, infant formula powders, follow-on milk formula, food for special medicinal purposes, meat products, soups, vegetable products, fruit juices, fruit products, breads, confectionary, cakes, sports supplements, nutritional supplements and the like.

In one embodiment, the composition includes a probiotic material. In one embodiment, the composition comprises a prebiotic material.

"Probiotic" refers to a microbial cell preparation, typically a bacterial cell preparation, that exerts a beneficial effect on the health or well-being of a host. They are described in Salminen et al (Trends Food Sci. Technol. 1999:10 107-110).

"Prebiotic" refers to a material or composition that can promote the growth of probiotic microbes or bacteria, especially bacterial growth in the mammalian gastrointestinal tract. Examples include oligosaccharides, dietary fibres, or mixtures thereof. Exemplary prebiotics are described in WO2011/039176, pages 12 to 15.

The invention also relates to pharmaceutical compositions which comprises pharmaceutical carriers.

As used herein, the term "pharmaceutical composition" refers to a therapeutically effective amount of the strain of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. In the case of the present invention, the term "therapeutically effective amount" should be taken to mean an amount of therapeutic which results in a clinically significant increase in proliferation of target cells, for example gut epithelial cells or skin epithelial cells.

As used herein, the term "adjuvant" means an agent that enhances the recipient's immune response to an immunogenic peptide or protein. Details of suitable adjuvant compositions are well known to those skilled in the art.

As used herein, the term "pharmaceutically acceptable carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions formulated or configured for oral administration and gastric transit are known in the art and include those described below:

Sathish et al (Int. J. Pharm. Sci. 2013; 258-269);
Kushal et al (Int. Res. J. Pharm. 2013, 4(3));
Philip et al (Oman Med J. 2010, 25(2));
Polymers for controlled drug delivery—Peter Tarcha (CRC Press, 21 Nov. 1990);
Pharmaceutical coating technology—Michael Aulton et al (Taylor & Francis 27 Oct. 1995);
European Patent No: 2418968 (Teagasc); and
European Patent No: 2097072 (RCSI).
Brayden et al. (European Journal of Pharmaceutical Sciences 79 (2015), 102-111.
Tambuwala et al. (Journal of Controlled Release 217 (2015) 221-227.
Zhang et al. Evaluation of alginate-whey protein microcapsules for intestinal delivery of lipophilic compounds in pigs (J. Sci. Food Agric. (2015).
Lamprecht et al. (Journal of Controlled Release 104 (2005) 337-346.
Hua et al. (Nanomedicine: Nanotechnology, Biology and Medicine 11 (2015) 1117-1132.
Drug Delivery: Fundamentals and Applications (Chapter 7, Oral Drug Delivery, Hillary and Brayden)

As used herein, the term "food" refers to a man-made food product including beverages, food additives and food supplements. Examples of foods include dairy products such as milk, yoghurt, cheese, cheese food, dairy powders, probiotic formulations, infant formula powders, follow-on milk formula, food for special medicinal purposes, meat products, soups, vegetable products, fruit juices, fruit products, breads, confectionary, cakes, sports supplements, nutritional supplements and the like.

Dosage

It is preferable that the strain or composition is administered at least one per week over at treatment period of at least 4 weeks, and preferably at least 5, 6, 7, 8, 9, 10, 11, 12, 14, 16, 18 or 20 week period. Preferably, the strain or composition is administered several times a week, and ideally once a day. Compositions of the invention generally comprise between $10^3$ and $10^{12}$ cfu of the strain of the invention per gram of dry weight of the composition. In one embodiment, the composition comprises $10^3$ and $10^{12}$ cfu, or $10^4$ and $10^{12}$ cfu, or 106 and $10^{10}$ cfu of the strain of the invention per gram of dry weight of the composition. A daily dose generally comprises between $10^3$ and $10^{12}$ cfu of the strain. In one embodiment, the daily dose comprises $10^3$ and $10^{12}$ cfu, or $10^4$ and $10^{12}$ cfu, or 106 and $10^{10}$ cfu of the strain.

Recombinant DNA Techniques and Reagents

The invention relates to an isolated *Bifidobacterium longum* APC1472 strain as deposited with the National Collection of Industrial, Food and Marine Bacteria under the Accession No. NCIMB 42795 on 1 Aug. 2017. The invention also relates to mutants and variants of the strain that are substantially identical to the deposited strain and exhibit the same weight modification functionality. This includes strains that are genetically engineered to alter the genome of the deposited strain (i.e. strained engineered for heterologous expression of nucleic acid), and variants obtained through natural genetic alterations such as spontaneous mutations, adaption and serial passage the term "engineered" as applied to a cell means genetically engineered using recombinant DNA technology, and generally involves the step of synthesis of a suitable expression vector (see below) and then transfecting (i.e. stably or transiently) the expression vector into a host cell (generally stable transfection). The term "heterologous expression" refers to expression of a nucleic acid in a host cell that does not naturally have the nucleic acid. Insertion of the nucleic acid into the heterologous host is performed by recombinant DNA technology. The term "heterologous in-situ expression" as applied to a bacterium of the invention means that the bacterium is capable of expressing the nucleic acid in-situ in the mammalian gut, especially in-situ expression when adhered to the epithelial layer of the gut. As used herein, the term "recombinant bacterium" or "transformed bacterium" refers to a bacterium comprising an exogenous nucleic acid stably integrated into the cellular genome. In another embodiment, the present invention provides a cell comprising a non-integrated (i.e., episomal) exogenous nucleic acid, such as a plasmid, cosmid, phagemid, or linear expression element, which comprises a sequence coding suitable for expression of an exogenous nucleic acid. In other embodiments, the present invention provides a cell line produced by stably transfecting a host cell with a plasmid comprising an expression vector of the invention.

As used herein, the term "expression vector" may be any suitable vector, including chromosomal, non-chromosomal, and synthetic nucleic acid vectors (a nucleic acid sequence comprising a suitable set of expression control elements) suitable for heterologous expression of a nucleic acid. Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, the Tad pilus encoding nucleic acid molecule is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. Nos. 5,589,466 and 5,973,972). In one embodiment, the DNA comprises an expression control sequence.

In one embodiment, the vector is suitable for heterologous expression of a nucleic acid in a bacterial cell. Examples of such vectors include expression vectors such as BlueScript (Stratagene), pIN vectors (Van Heeke & Schuster, 1989, J Biol Chem 264, 5503-5509), pET vectors (Novagen, Madison, Wis.) and the like. In one embodiment, the expression vector may also or alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed., 1987, Current Protocols in Molecular Biology, Greene Publishing and Wiley InterScience New York; and Grant et al., 1987, Methods in Enzymol 153, 516-544). In other embodiments, the expression vector is suitable for expression in baculovirus-infected insect cells. (Kost, T; and Condreay, J P, 1999, Current Opinion in Biotechnology 10 (5): 428-33.) Expression control sequences are engineered to control and drive the transcription of genes of interest, and subsequent expression of proteins in various cell systems. Plasmids combine an expressible gene of interest with expression control sequences (i.e. expression cassettes) that comprise desirable elements such as, for example, promoters, enhancers, selectable markers, operators, etc. In an expression vector of the invention, Tad pilus-encoding nucleic acid molecules may comprise or be associated with any suitable promoter, enhancer, selectable marker, operator, repressor protein, polyA termination sequences and other expression-facilitating elements.

"Promoter" as used herein indicates a DNA sequence sufficient to direct transcription of a DNA sequence to which it is operably linked, i.e., linked in such a way as to permit transcription of the exogenous nucleotide sequence when the appropriate signals are present. The expression of a nucleotide sequence may be placed under control of any promoter or enhancer element known in the art. Examples of such elements include strong expression promoters (e.g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters). In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules of the invention may also be operably linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a fluorescent protein marker are made visible, and are thus selectable. Embodiments include beta-lactamase (bla) (beta-lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene).

In certain embodiments, the vector comprises one or more selectable marker genes selected from the group consisting of bla, bls, BSD, bsr, Sh ble, hpt, tetR, tetM, npt, kanR and pac. In other embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), or yellow fluorescent protein (YFP).

For the purposes of this invention, gene expression in eukaryotic cells may be tightly regulated using a strong promoter that is controlled by an operator that is in turn regulated by a regulatory protein, which may be a recombinant "regulatory fusion protein" (RFP). The RFP consists essentially of a transcription blocking domain, and a ligand-binding domain that regulates its activity. Examples of such expression systems are described in US20090162901A1, which is herein incorporated by reference in its entirety.

As used herein "operator" indicates a DNA sequence that is introduced in or near a gene in such a way that the gene may be regulated by the binding of the RFP to the operator and, as a result, prevents or allow transcription of the gene of interest, i.e. a nucleotide encoding a polypeptide of the invention. A number of operators in prokaryotic cells and bacteriophage have been well characterized (Neidhardt, ed., *Escherichia coli* and *Salmonella*; Cellular and Molecular Biology 2d. Vol 2 ASM Press, Washington D.C. 1996). These include, but are not limited to, the operator region of the LexA gene of *E. coli*, which binds the LexA peptide, and the lactose and tryptophan operators, which bind the repressor proteins encoded by the LacI and trpR genes of *E. coli*. These also include the bacteriophage operators from the lambda PR and the phage P22 ant/mnt genes, which bind the repressor proteins encoded by lambda cI and P22 arc. In some embodiments, when the transcription blocking domain of the RFP is a restriction enzyme, such as NotI, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

In an exemplary cell expression system, cells are engineered to express the tetracycline repressor protein (TetR) and a protein of interest is placed under transcriptional control of a promoter whose activity is regulated by TetR. Two tandem TetR operators (tetO) are placed immediately downstream of a CMV-MIE promoter/enhancer in the vector.

Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription then translation (expression) of the protein of interest occurs. (See, e.g., U.S. Pat. No. 7,435,553, which is herein incorporated by reference in its entirety.) The vectors of the invention may also employ Cre-lox recombination tools to facilitate the integration of a gene of interest into a host genome. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. (See, e.g. Araki et al., 1995, PNAS 92:160-4; Nagy, A. et al., 2000, Genesis 26:99-109; Araki et al., 2002, Nuc Acids Res 30(19):e103; and US20100291626A1, all of which are herein incorporated by reference). In another recombination strategy, yeast-derived FLP recombinase may be utilized with the consensus sequence FRT (see also, e.g. Dymecki, S. M., 1996, PNAS 93(12): 6191-6196).

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Methods

Bacterial Strains Supernatants Preparation.

Different *Lactobacillus* and *Bifidobacterium* strains provided by the bacterial strains collection of the APC Microbiome Institute and Teagasc Research Center (Cork, Ireland) were routinely cultured in anaerobic conditions in Man Rogosa Sharpe (MRS) agar medium (Difco Laboratories, USA) (for *Bifidobacterium* strains medium was supplemented with cysteine hydrochloride (0.05% w/v). A single colony from each strain was inoculated in MRS broth medium and incubated overnight under anaerobic conditions at 37° C. A subculture was then carried out by adjusting the OD600 to 0.05 and incubated overnight under anaerobic conditions at 37° C. for 14 hours approx. Bacterial cell pellets were collected by centrifugation at 5000 rpm for 15 min at 4° C., washed twice, concentrated in assay medium (lx Hanks balanced salt solution (HBSS) containing 20 mM HEPES) (Gibco, UK) and incubated for 4 hours under culture conditions. Finally, bacterial supernatants were collected by centrifugation at 5000 rpm for 15 min at 4° C., filtered by 0.2 μm and pH was adjusted to 7.4 by addition of NaOH 1M. All supernatants were diluted 1:2 in assay medium before testing them on the cells.

GHS-R1a Internalisation Assay

The potential of the bacteria supernatants to modulate the ghrelin receptor was analyzed by measuring their effect on the receptor internalization using human embryonic kidney cells (Hek293a) (Invitrogen, Ireland) stably expressing the human GHS-R1a receptor with a C-terminal enhanced green fluorescent protein (EGFP) tag. Hek-GHSR1a-EGFP cells were seeded in a 96-well microtiter plate at 3×104 cells/well and incubated for 48 hours in Dulbecco's Modified Eagle's Medium-high glucose (DMEM) (Sigma-Aldrich, Ireland) supplemented with 10% fetal bovine serum (FBS) (Sigma-Aldrich) and 1% non-essential amino acids (Gibco) at culture conditions (5% CO2-humidified atmosphere at 37° C.). For the last 24 hours medium was replaced with serum free DMEM-high glucose medium. Cells were incubated for 1 hour with 1:2 diluted bacterial strains supernatants prepared as described above. Finally, cells were fixed with 4% paraformaldehyde in phosphate buffer saline (PBS) (Sigma-Aldrich) for 20 min and washed with 1×PBS. Ghrelin (0.5 μM) (Innovagen, Sweeden) was used as positive control. In addition, treatment with the inverse agonist, [D-Arg1, D-Phe5, D-Trp7,9, Leu11]-substance P (SP-analogue) (0.5

μM) (Tocris, R&D Systems, UK), which inhibits GHS-R1a receptor constitutive activity and enhances GHS-R1a receptor membrane expression, was also carried out. Moreover, effect of the bacterial strains supernatants on the ghrelin-mediated GHS-R1a internalization was also analyzed by exposing the cells to the supernatants for 1 hour followed by exposure to the agonist ghrelin for 1 hour. Cells were then imaged in PBS using the GE Healthcare IN Cell Analyzer 1000 (GE Healthcare, UK). Receptor GHS-R1a-EGFP trafficking was quantified by analyzing the EGFP fluorescence perinuclear intensity using the InCell Analyzer Developer Toolbox V1.6 software (GE Healthcare). Briefly, a total of 15 fields were analyzed using the automated software across 3 independent images. Considering that the GHS-R1a-EGFP receptor accumulates in the perinuclear space after internalization, a target segmentation based on the fluorescence intensity of perinuclear space was used. Data are normalized to the maximum expected receptor internalization obtained upon treatment with the agonist ghrelin, analyzed and depicted using GraphPad Prism software (PRISM 5.0; GraphPAD Software Inc., USA).

β-Arrestin-1 Recruitment Analysis

PathHunter® eXpress GHSR U2OS β-Arrestin-1 GPCR Assay (Discoverx, UK) was used to investigate the effect of *B. longum* APC1472 supernatant on the ghrelin receptor activation by monitoring the β-Arrestin-1 proteins recruitment. The assay was performed according to the manufacturer's protocol with some modifications. Briefly, provided cells were incubated for 48 hours at culture conditions. Then, cells were incubated with the bacteria strain supernatant (1:2 diluted in assay medium: 1×HBSS, 20 mM HEPES) for 1 hour. The agonist ghrelin (0.5 μM) was included as a positive control. Moreover, ghrelin receptor antagonist activity of *B. longum* APC1472 was investigated by exposure to the bacteria supernatant for 1 hour followed by exposure to ghrelin for 1 hour. SP-analogue (0.5 μM), which is known to have both antagonist and inverse agonist properties, was also included as control. Finally, 55 μl detection reagents were added, cells were incubated for 60 min at room temperature and luminescence was read with the Synergy 2 (Biotek, UK). Data are normalized to the maximum expected β-Arrestin-1 proteins recruitment obtained upon treatment with the agonist ghrelin, analyzed and depicted using GraphPad Prism software (PRISM 5.0; GraphPAD Software Inc., USA).

Mice and Diets.

Five-week-old male C57BL/6 mice (Harlan Laboratories, UK) (40 mice, n=10 per group) were housed in groups of 2 mice per cage in standard holding cages with free access to food and water at the animal care facility of University College Cork. The holding room temperature (21±1° C.) and humidity (55±10%) were controlled under a 12 h light/dark cycle (lights on 7.00 AM, lights off 7.00 PM). The mice were fed a low-fat diet (LFD) (10% fat (kcal/100 g), D12450B, Research Diet, USA) or fed a high-fat diet (HFD) (45% fat (kcal/100 g), D12451, Research Diet, USA) for 16 weeks. Food intake was recorded once per week and calculated on the basis of two mice per cage and five cages per group. The data were reported as cumulative food intake per mouse. Body weight was weekly monitored for 15 weeks. All experiments were approved by the Animal Experimentation Ethics Committee at University College Cork and carried out in accordance with the relevant guidelines—200 European Directive 2010/63/EU.

Probiotic Administration

*Bifidobacterium longum* APC1472 was grown anaerobically in MRS medium as previously described above. Bacterial cell pellet was washed and concentrated in sterile PBS containing 25% Glycerol (vol/vol) to an end concentration of 7.5×109 CFU/mL, aliquoted and stored at −80° C. Aliquots were daily defrosted just prior the start of the dark phase and diluted to 2×108 CFU/mL in drinking water. Water intake was monitored throughout the experiment. Mice consumed ~6×108 CFU daily in drinking water. Probiotic aliquots were freshly prepared every week. Drinking water containing an equivalent end concentration of sterile PBS (2% vol/vol) and glycerol (0.5% vol/vol) was administered to control mice. Water was replaced for free probiotic/vehicle water every morning.

Glucose Tolerance Test.

Glucose tolerance was assessed after 15 weeks treatment accordingly to Suez et al., (Suez, Korem et al. 2014) with modifications. Briefly, mice were fasted for 7 hours during the light phase, with free access to water. Glucose levels were measured from the tail vein blood using a glucometer (Bayer, UK) immediately before and 15, 30, 60, 90 and 120 min after intra-peritoneal injection of glucose (1 g/kg of body weight).

Tissue Sampling

Mice were euthanized by decapitation. Trunk blood was collected in tubes containing 25 μM DPPIV inhibitor, 2× protease inhibitor cocktail (Roche) (dilute in PBS) and 0.1% Na2EDTA for an expected blood volume of 400 μL, centrifugated at 3500 g for 15 min at 4° C. and placed on dry ice until storage at −80° C. for further analysis. Adipose depots (epididymal, subcutaneous, mesenteric and retroperitoneal) were precisely dissected and weighed. The intestinal segments (ileum, cecum, and colon) were also dissected and collected. Whole brain was collected and placed for 8-10 sec into pre-cooled isopentane. Macropunches of hypothalamus were taken for RNA expression analysis. All tissues were pre-cooled on dry ice and finally stored at −80° C. for further analysis.

Biochemical Analysis

Plasma insulin and leptin were analyzed by ELISA using the MILLIPLEX® MAP Mouse Metabolic Hormone Magnetic Bead Panel (MMHMAG-44K, Millipore, USA) accordingly to manufacturer's instructions. Plasma ghrelin levels were analyzed using the Rat/Mouse Ghrelin (Total) ELISA Kits (Millipore). Triglycerides levels were analyzed with a Triglyceride Quantification Kit (Abcam Ltd, UK) accordingly to manufacturer's instructions. Corticosterone levels were assayed using a commercially-available ELISA kit (Corticosterone EIA Kit, Enzo Life Sciences, USA) according to manufacturer instructions.

RNA Isolation and Quantitative Real-Time PCR

Hypothalamus and adipose tissue total RNA was extracted using the mirVana™ miRNA Isolation kit (Ambion/Life Technologies, UK) and RNeasy@ Lipid Tissue Mini Kit (Quiagen, UK) respectively with DNase treatment (Turbo DNA-free, Ambion/life Technologies) according to the manufacturers recommendations. Analysis of RNA expression levels was carried as previously described (RM, Pusceddu et al. 2013). Briefly, equal amounts of RNA were first reverse transcribed to cDNA using High Capacity cDNA Reverse Transcription Kit (Applied Biosystems, Life Technologies, CA). Real-time PCR was performed using TaqMan Universal Master Mix II, no UNG. Mouse β-actin control (DQ) mix Probe dye: VIC-MGB (Applied Biosystems) was used as an endogenous control. Cycle threshold (Ct) values were recorded, normalized to its endogenous control and transformed to relative gene expression value using the 2-ΔΔCt method (Livak and Schmittgen 2001). Each sample was analyzed in triplicate for both target gene and endogenous control using the 7300 System SDS Software (Applied Biosystems, Life Technologies).

Gut Microbiota Analysis

Cecal DNA was isolated using the QIAamp Fast DNA Stool Mini kit (Quiagen) accordingly as previously described and kept at −20° C. until further analysis (Burokas et al 2017). Isolated DNA was quantified on a NanoDrop ND2000 spectrophotometer (Thermo Scientific, DE) and used for 16S ribosomal RNA sequencing by Illumina MiSeq System (Illumina Inc., USA) accordingly to the manufacturer's instructions. Briefly, PCR amplicons (primers for V3-V4 hypervariable region of the 16S rRNA gene: F (5'-TCGTCGGCAGCGTCAGATGTGTATAAGA-GACAGCCTACGGGNGGCWGCAG-3') (SEQUENCE ID NO: 2) and R (5'-GTCTCGTGGGCTCG-GAGATGTGTATAAGAGACAGGACTACH VGGGTATCTAATCC-3')) (SEQUENCE ID NO: 3) were purified and libraries prepared as previously described (Burokas et al., 2017). Samples were sequenced at Clinical-Microbiomics, Denmark on the Illumina MiSeq platform using a 2×300 bp kit. After sequencing, reads were assembled, processed and analyzed as previously described (Burokas, Arboleya et al. 2017).

Statistical Analysis

Statistical analysis was performed using SPSS software (IBM SPSS statistics 22). Normality of the data was tested by Shapiro-Wilk test. Ghrelin receptor modulation data was analyzed with non-parametric multiple comparisons Kruskal-Wallis test followed by Bonferroni adjustment of p-values. In vivo data analysis was performed with a two-way ANOVA followed by LSD post hoc test (normal distributed data) or non-parametric multiple comparisons Kruskal-Wallis test with Bonferroni adjustment of p-values (non-normal distributed data). Body weight changes and glucose level over time were analyzed with Repeated Measures ANOVA followed by LSD post hoc test. Level of significant in all analysis was $\alpha=0.05$ and all tests were two-tailed test. All graphs represent the mean±SEM from N independent experiments (see figure legends for statistical details for each experiment). Statistical significances are subsequently depicted as follows: *indicating $p \leq 0.05$, indicating $p \leq 0.01$ or *indicating $p \leq 0.001$ Antibiotic Susceptibility Antibiotic susceptibility was tested with VetMIC plates Lact-1 and Lact-2 supplied from SVA (National Veterinary Institute, Uppsala, Sweden). The procedure followed the international standard of antibiotic testing for Bifidobacteria (ISO 10932:2010/IDF 223:2010). Colonies were suspended to OD 0.16-0.2 (at 625 nm) in LSM-Cys media (90% (v/v) ISO-sensitest (Ocon chemicals), 10% (v/v) MRS broth (Difco laboratories, Detroit, MI), supplemented with 0.3 g/L L-Cysteine (Sigma Aldrich) from strains grown on RCM agar anaerobically incubated at 37° C. for 48-72 h. Attained cell density corresponding to $3 \times 10^8$ CFU/ml was further diluted 1000 fold to a cell density of $3 \times 10^5$ CFU/ml. One hundred of cell suspension was aliquoted into 96-well plates within 30 min with a multichannel pipette to give $\sim 3 \times 10^4$ CFU/well. Plates were incubated at 37° C. for 48 h. After 48 h the plates were read visually. MICs were determined as 80% or more reduction in pellet, compared to positive control lane. Borderline cases were interpreted by visual examples from "Methods for Antimicrobial Susceptibility Testing of Anaerobic Bacteria: Approved Standard" (CLSI, 7th edition).

Summary of Results

Figure 1A:
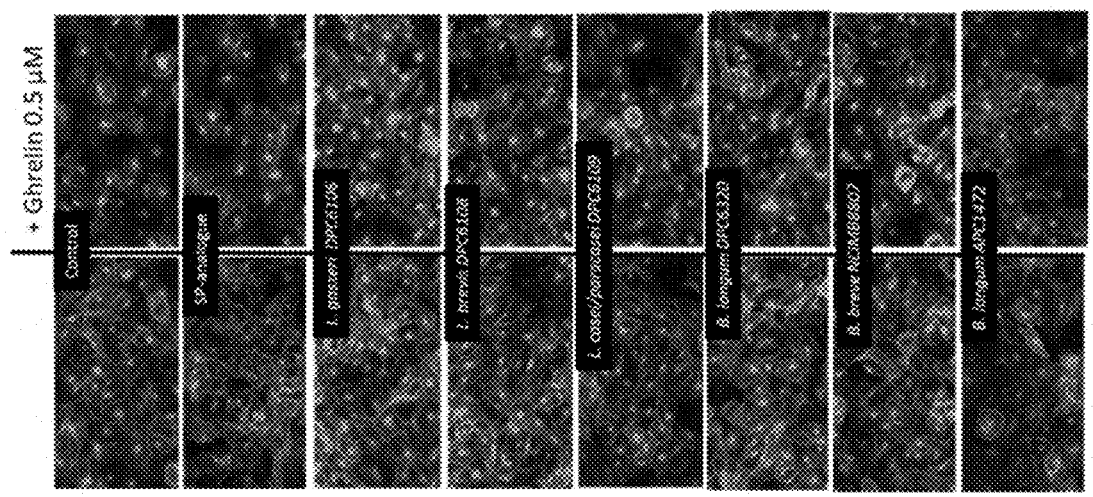
Figure 1C:
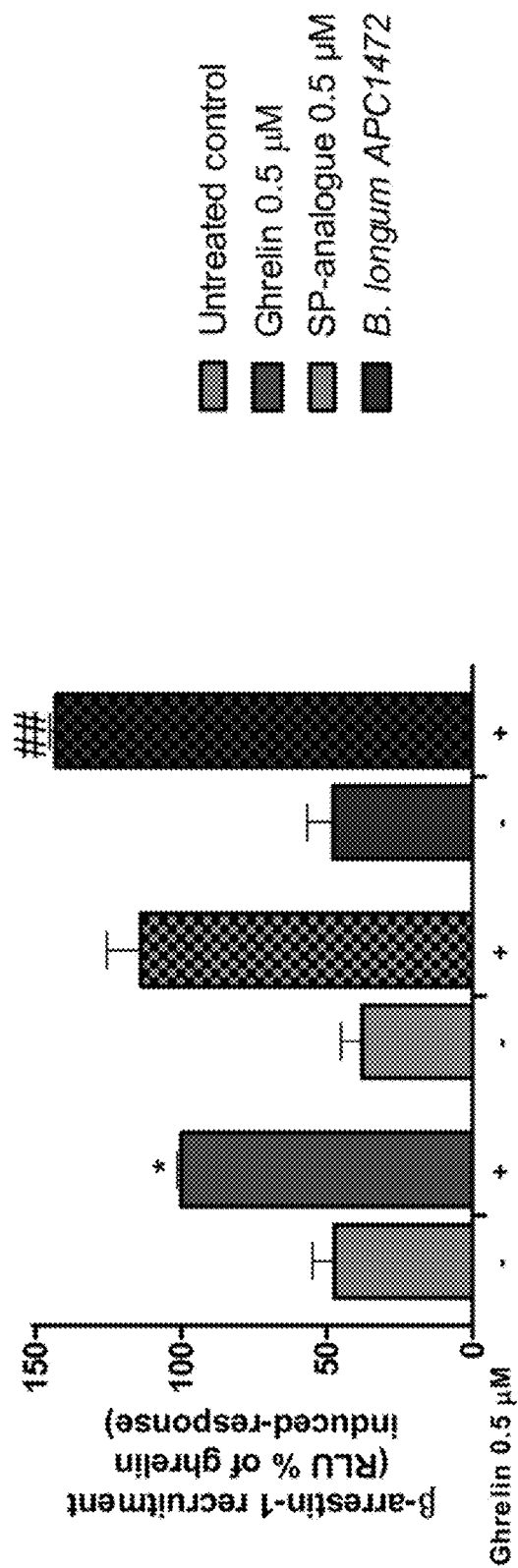

1. Supernatant from *B. longum* APC1472 culture showed capability to significantly reduce the basal level of the ghrelin receptor internalization as well as the ghrelin-mediated receptor internalization process (FIG. 1A). The effect of this bacterial strain supernatant was even stronger than the one observed for the inverse agonist SP-analogue at 0.5 µM, which it did not block the ghrelin-mediated receptor internalization (FIG. 1A). None of the others bacterial strains supernatants investigated showed any effect. β-arrestin protein recruitment, which are the most widely standard adaptor for GPCRs internalization (Lefkowitz 1998). Although no effect was observed on the basal level of β-arrestin recruitment, a significant potentiation effect of ghrelin was observed when cells were first exposed to *B. longum* APC1472 supernatant (FIG. 1B). Exposure to SP-analogue decreased the levels of β-arrestin recruitment and potentiated ghrelin-mediated response but these effects were not statistically significant at the assayed concentration (0.5 µM).

Figure 2B:
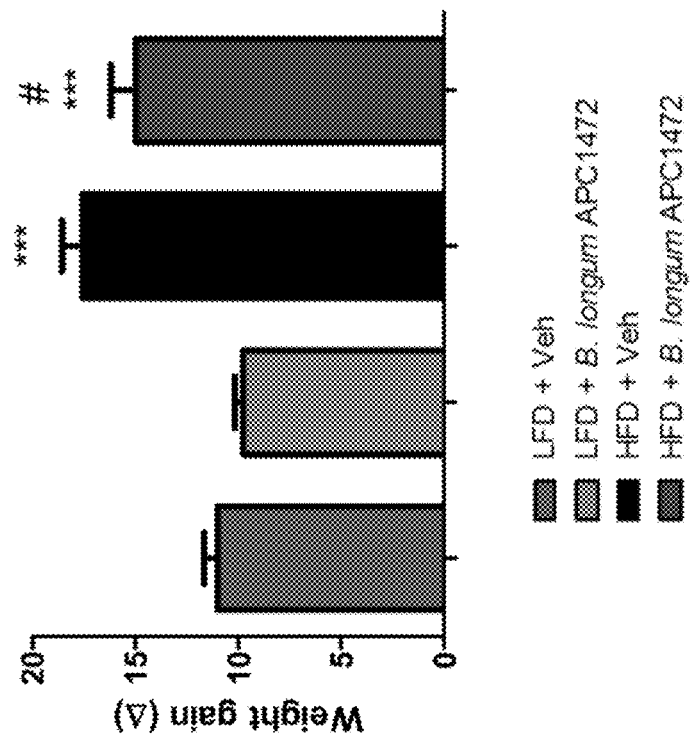
FIGS. 2A-2F are graphs directed to the effects of *Bifidobacterium longum* APC1472 on body weight and fat depots accumulation.
Figure 2A:
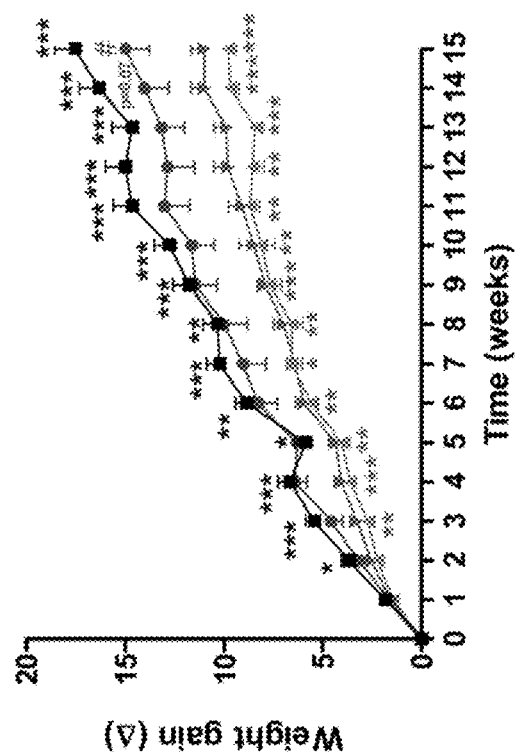
Figure 2D:
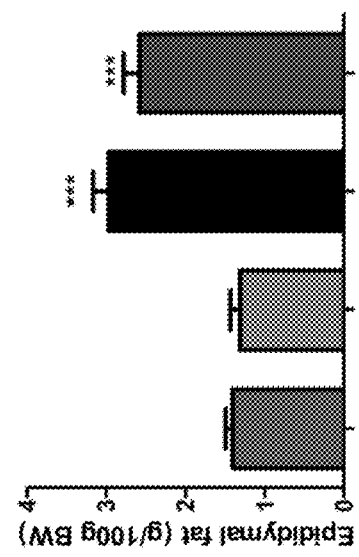
Figure 2F:
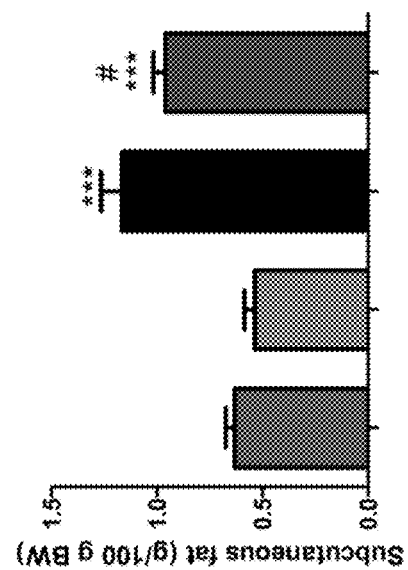
Figure 2C:
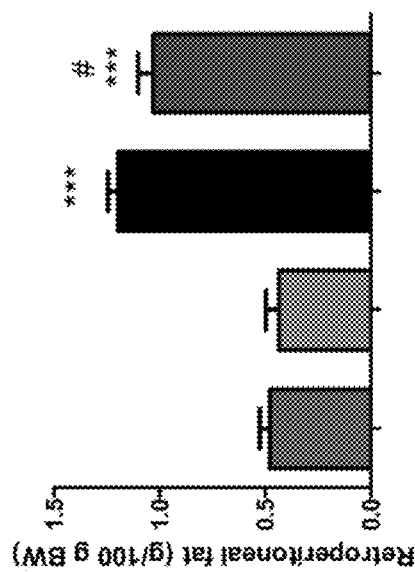
Figure 2E:
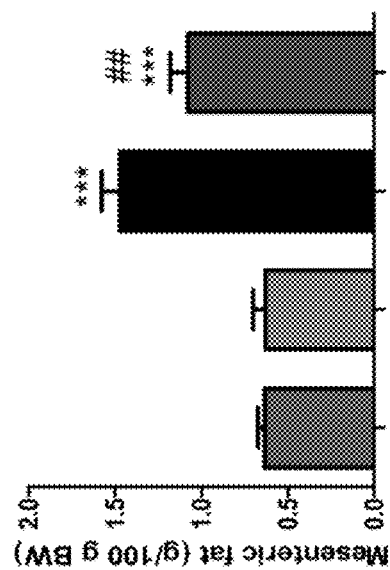

2. It is well known that HFD feeding promotes weigh gain and adiposity leading to obesity (Schneeberger, Everard et al. 2015). Here we found that a 45% fat (kcal/100 g) diet led to a significant increased body weight after 2 weeks of treatment (FIG. 2A). Notably, *B. longum* APC1472 treatment decreased the body weight gain after 14 weeks (trend; p=0.07) and 15 weeks of dietary intervention in HFD-fed mice without changes in food intake (FIG. 2B). Furthermore, administration of *B. longum* APC1472 also reduced fat depots accumulation in HFD-fed mice (visceral, retroperitoneal and subcutaneous) (FIG. 2C, D, E).

Figure 3D:
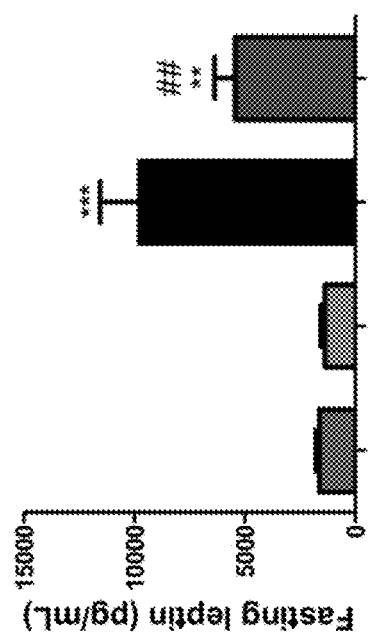
Figure 3E:
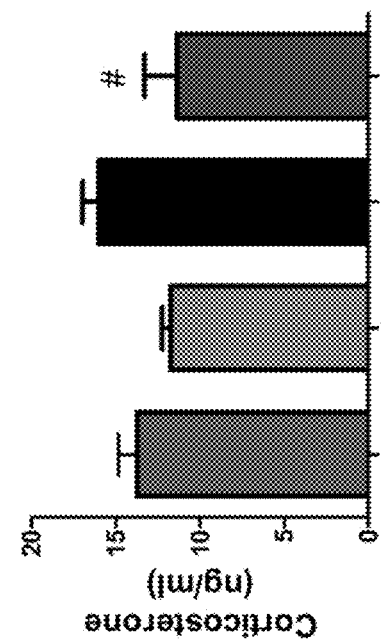
Figure 3F:
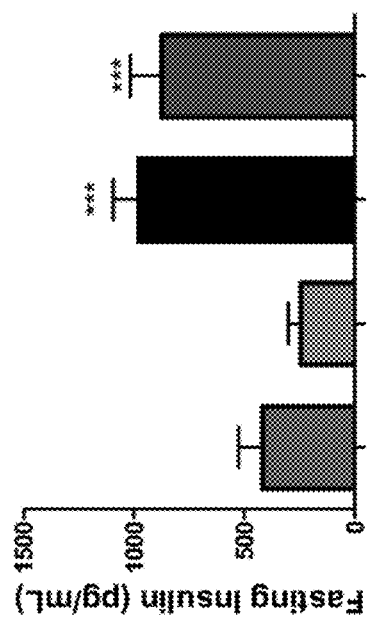
Figure 3G:
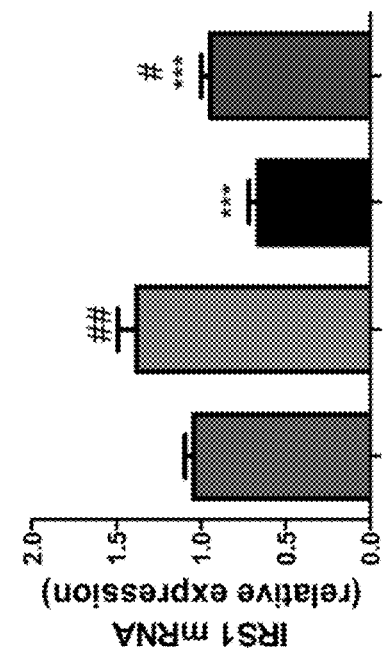

3. *B. longum* APC1472 treatment completely normalized glucose levels after 15' of glucose administration in HFD-fed mice (FIG. 3A). Moreover, *B. longum* APC1472 treatment reduced glucose-stimulated glycemia as shown by a significant decreased area under the curve (AUC) (FIG. 3B). In addition, *B. longum* APC1472 treated groups showed reduced non-fasting insulin levels in LFD-fed mice (FIG. 3C). However, not significant *B. longum* APC1472 treatment effects were found for fasting insulin levels (FIG. 3D). Furthermore, *B. longum* APC1472 treatment decreased fasting leptin levels (FIG. 3E) which, in addition to be in line with *B. longum* APC1472 effects on fat depots, may be involved on glucose homeostasis improvement. Interestingly, *B. longum* APC1472 treatment led to a significant increase in epididymal insulin receptor substrate 1 (IRS-1) expression in both LFD-fed and HFD-fed mice (FIG. 3F). Finally, we found a significant decrease of stress-induced corticosterone circulating levels in HFD-fed mice, which may also impact on glucose homeostasis (FIG. 3G).

4. *B. longum* APC1472 treatment reduced the expression of the orexigenic peptides Agouti-related protein (AgRP) and neuropeptide Y (NPY) in both LFD-fed and HFD-fed mice (FIG. 4A, B). Furthermore, *B. longum* APC1472 treatment trended to reduce leptin receptor expression (p=0.06) in HFD-fed mice (FIG. 4C). Moreover, when comparing only the HFD-fed mice groups, *B. longum* APC1472 treatment also trended (p=0.07) to decrease the expression of the ghrelin receptor (FIG. 4D).

Figure 5:
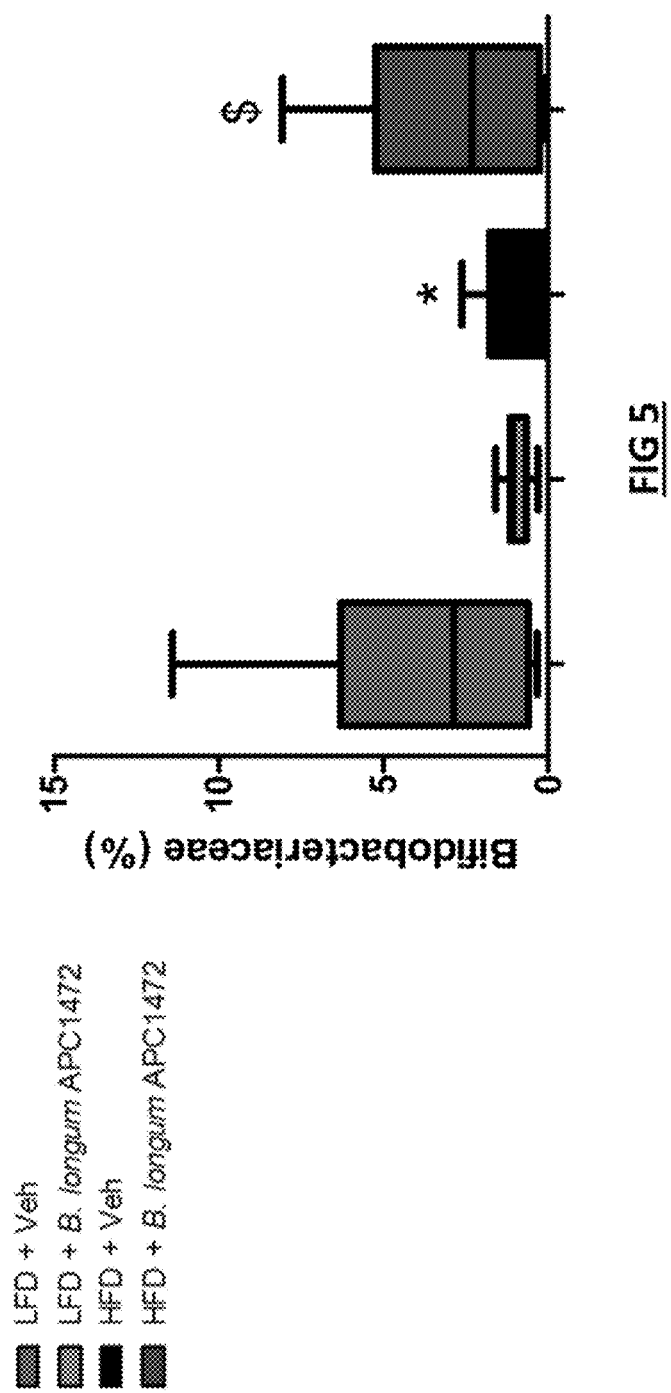
FIG. 5 is a graph showing *Bifidobacterium longum* APC1472 effects on caecal microbiota B. *longum* APC1472 treatment restored the HFD-associated decrease in *Bifidobacterium* at the family level.

5. *B. longum* APC1472 treatment trended to restore the HFD-associated decrease in *Bifidobacterium* at the family level (FIG. 5).

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

ANNEX 1 16s Ribosomal RNA amplicon
sequence for *Bifidobacterium Longum* APC1472
(SEQUENCE ID NO: 1)
CCGGTCTCAGTTCGGATCGCAGTCTGCAACTCGACTGCGTGAAGGCGGAG

TCGCTAGTAATCGCGAATCAGCAACGTCGCGGTGAATGCGTTCCCGGGCC

TTGTACACACCGCCCGTCAAGTCATGAAAGTGGGCAGCACCCGAAGCCGG

TGGCCTAACCCCTTGTGGGATGGAGCCGTCTAAGGTGAGGCTCGTGATTG

GGACTAAGTCGTAACAAGGTAGCCGTACCGGAAGGTGCGGCTGGATCACC

TCCTTTCTACGGAGAATTCAGTCGGATGTTCGTCCGACGGTGTGCGCCCC

GCGCGTCGCATGGTGCGATGGCGGCGGGGTTGCTGGTGTGGAAGACGTCG

TTGGCTTTGCCCTGCCGGTCGTGCGGTGGGTGCCGGGGTGGTATGGATGC

GCTTTTGGGCTCCCGGATCGCCACCCCAGGCTTTTTGCCTGGCGCGATTC

GATGCCCGTCGTGCCTGGGGGCCGGCCGTGTGCCGGCGCGATGGCGTGGC

GGTGCGTGGTGGCTTGAGAACTGGATAGTGGACGCGAGCAAAACAAGGGT

TTTTGAATCTTTGTTTTGCTGTTGATTTCGAATCGAACTCTATTGTTCGT

TTCGATCGTTTTGTGATCATTTTTAGTGTGATGATTTGTCGTCTGGGAAT

TTGCTAGAGGAATCTTGCGGCCATGCACTTTCGTGGTGTGTGTTGCTTGC

AAGGGCGTATGGTGGAT

---

The invention claimed is:

1. A composition comprising at least $10^6$ CFU per gram of the composition of the isolated *Bifidobacterium longum* APC1472 strain as deposited with the National Collection of Industrial, Food and Marine Bacteria under the Accession No. NCIMB 42795 on 1 Aug. 2017.

2. The composition of claim 1, selected from a food or beverage product or a nutritional supplement.

3. The composition of claim 1, comprising a probiotic material or a prebiotic material.

4. The composition of claim 1, including an additional probiotic bacterium.

5. The composition of claim 1, in which the isolated *Bifidobacterium longum* APC1472 strain is viable or non-viable.

6. A pharmaceutical composition comprising at least $10^6$ CFU per gram of the composition of the isolated *Bifidobacterium longum* APC1472 strain as deposited with the National Collection of Industrial, Food and Marine Bacteria under the Accession No. NCIMB 42795 on 1 Aug. 2017, and a suitable pharmaceutical excipient.

7. The pharmaceutical composition of claim 6, in a unit dose form suitable for oral administration.

8. The pharmaceutical composition of claim 6, configured for targeted release in the intestine.

9. The composition of claim 1 in which the strain is in a dried or lyophilised form.

10. A method of producing a culture supernatant from a culture of the isolated *Bifidobacterium longum* APC1472 strain deposited with the National Collection of Industrial, Food and Marine Bacteria under the Accession No. NCIMB 42795, the method comprising a step of culturing the isolated strain and separating the supernatant from the culture, thereby producing the culture supernatant.

11. A method of producing an extract from cells of the isolated *Bifidobacterium longum* APC1472 strain deposited with the National Collection of Industrial, Food and Marine Bacteria under the Accession No. NCIMB 42795, the method comprising a step of lysing the cells of the isolated strain and separating the extract of the lysed cells, thereby producing the extract.

12. The pharmaceutical composition of claim 6 comprising at least $10^8$ CFU per gram of the composition of the isolated *Bifidobacterium longum* APC1472 strain.

* * * * *

SEQUENCE LISTING

<160> NUMBER OF SEQ ID NOS: 3

<210> SEQ ID NO 1
<211> LENGTH: 717
<212> TYPE: DNA
<213> ORGANISM: Bifidobacterium longum
<220> FEATURE:
<221> NAME/KEY: rRNA
<222> LOCATION: (1)..(717)
<223> OTHER INFORMATION: 16S rRNA FRAGMENT

<400> SEQUENCE: 1
ccggtctcag ttcggatcgc agtctgcaac tcgactgcgt gaaggcggag tcgctagtaa    60
tcgcgaatca gcaacgtcgc ggtgaatgcg ttcccgggcc ttgtacacac cgcccgtcaa   120
gtcatgaaag tgggcagcac ccgaagccgg tggcctaacc ccttgtggga tggagccgtc   180
taaggtgagg ctcgtgattg ggactaagtc gtaacaaggt agccgtaccg gaaggtgcgg   240
ctggatcacc tcctttctac ggagaattca gtcggatgtt cgtccgacgg tgtgcgcccc   300
gcgcgtcgca tggtgcgatg gcggcggggt tgctggtgtg gaagacgtcg ttggctttgc   360
cctgccggtc gtgcggtggg tgccggggtg gtatggatgc gcttttgggc tcccggatcg   420 ccacccagg cttttgcct ggcgcgattc gatgcccgtc gtgcctgggg gccggccgtg   480
tgccggcgcg atggcgtggc ggtgcgtggt ggcttgagaa ctggatagtg gacgcgagca   540
aaacaagggt ttttgaatct ttgttttgct gttgatttcg aatcgaactc tattgttcgt   600
ttcgatcgtt ttgtgatcat ttttagtgtg atgatttgtc gtctgggaat ttgctagagg   660
aatcttgcgg ccatgcactt tcgtggtgtg tgttgcttgc aagggcgtat ggtggat     717

<210> SEQ ID NO 2
<211> LENGTH: 50
<212> TYPE: DNA
<213> ORGANISM: Artificial Sequence
<220> FEATURE:
<223> OTHER INFORMATION: PCT FORWARD PRIMER
<220> FEATURE:
<221> NAME/KEY: misc_feature
<222> LOCATION: (42)..(42)
<223> OTHER INFORMATION: n is a, c, g, or t

<400> SEQUENCE: 2
tcgtcggcag cgtcagatgt gtataagaga cagcctacgg gnggcwgcag              50

```
<210> SEQ ID NO 3
<211> LENGTH: 55
<212> TYPE: DNA
<213> ORGANISM: Artificial Sequence
<220> FEATURE:
<223> OTHER INFORMATION: PCR REVERSE PRIMER

<400> SEQUENCE: 3
gtctcgtggg ctcggagatg tgtataagag acaggactac hvgggtatct aatcc        55
```